United States Patent

Widerström et al.

[11] Patent Number: 5,535,741
[45] Date of Patent: Jul. 16, 1996

[54] FACE MASK

[75] Inventors: Carin Widerström, Höllviken; Jan Karlsson, Hjärup, both of Sweden

[73] Assignee: Astra Aktiebolag, Sodertalje, Sweden

[21] Appl. No.: 313,427

[22] Filed: Sep. 27, 1994

[30] Foreign Application Priority Data

Sep. 27, 1993 [SE] Sweden ............................. 9303155

[51] Int. Cl.⁶ ...................................... A62B 18/02
[52] U.S. Cl. ...................... 128/206.21; 128/206.28; 128/205.25
[58] Field of Search ..................... 128/716, 730, 128/201.22, 201.23, 201.24, 202.28, 202.29, 205.25, 203.11, 206.12, 206.21, 206.24, 206.28, 206.19, 206.26, 203.29

[56] References Cited

U.S. PATENT DOCUMENTS

| 3,042,035 | 7/1962 | Coanda | 128/206.24 |
| 4,832,015 | 5/1989 | Nowacki et al. | 128/205.23 |
| 5,012,803 | 5/1991 | Foley et al. | 128/200.23 |

FOREIGN PATENT DOCUMENTS

| 0344879 | 12/1989 | European Pat. Off. . |
| 0384050 | 8/1990 | European Pat. Off. . |
| 2230456 | 10/1990 | United Kingdom . |
| WO93/01854 | 2/1993 | WIPO . |

OTHER PUBLICATIONS

McCarthy, "Use of a Chamber Device and Mask in Young Children with Asthma".

Primary Examiner—Edgar S. Burr
Assistant Examiner—Eric P. Raciti
Attorney, Agent, or Firm—Fish & Richardson

[57] ABSTRACT

A face mask is provided which is adapted to be mounted an inhalation device, e.g., an inhaler or spacer, having a body. The mask includes an annular adaptor part which is to be connected to one end of the body, and a funnel-shaped face engaging portion having a narrow end that is joined to one end of the adaptor part. The wide end of the face engaging portion has a free edge that is adapted to engage the face of an infant around the infant's mouth and at least a part of the infant's nose, and is resilient so that it is adaptable to the shape of the infant's face. The free edge of the wide end of the face engaging part is provided substantially entirely in a plane which forms an angle of about 10°–25° with a plane perpendicular to the extended longitudinal axis of the adaptor part.

23 Claims, 1 Drawing Sheet

FACE MASK

BACKGROUND OF THE INVENTION

The present invention relates to a face mask for infants adapted to be mounted on an inhaler device, e.g., an inhaler used to deliver medicaments for the treatment of bronchial diseases such as asthma.

When dealing with bronchial diseases among children and infants, it is difficult to make the patient inhale the therapeutic substances necessary for treatment. When asthma makes its debut among infants and young children, typically at 8 months to 2.5 years, it is especially difficult to make the infant inhale the prescribed medical substances in the proper way. An infant has a limited lung capacity and the force of the infant's breath during inhalation (inhalation flow) is thus limited. This is even more apparent when the infant is suffering from asthma or other bronchial diseases. Parents also desire that the devices used for inhalation be as flexible as possible, as it is difficult to position the inhaler in a way that will allow proper inhalation by an infant.

It is known in the art to use stationary inhalation devices having expensive and complicated face masks which adapt the device for use on infants. Use of a stationary device is inconvenient both for the infant and for the parents as they are bound to these stationary devices which are often placed in hospitals. As the inhalation capacity of an infant is limited, the administration will be time consuming, which of course also is inconvenient.

Thus, inhalation therapy is typically accomplished through the use of portable metered-dose inhalers. A metered-dose aerosol inhaler includes a holder for a medicament dispenser and an extended body, which in the technical field of inhalers normally is called a "spacer" or inhalation chamber, having an outlet provided at the end remote from the dispenser. An inhalation/exhalation valve, e.g., a one-way valve, is typically provided adjacent to the outlet, and at the outlet opening a mouthpiece is provided. When such a device is used by older children or adults the mouthpiece is inserted between the teeth and the lips are closed around the mouthpiece. It is however not possible for an infant to hold such a mouthpiece between its lips. Moreover, these devices are constructed to be used by older children who have large lung capacity and who can inhale more forcefully. The inhalation/exhalation valves provided typically require a certain inhalation flow, which an infant is unable to generate, to open properly. Therefore, for satisfactory inhalation to be achieved by infants, these inhalation devices generally must be provided with a face mask.

Face masks have thus been proposed which include an annular adaptor part which is to be connected to one end of the body of the inhalation device or spacer, and a face engaging portion which is joined with one end of the of the adaptor part. EP 0 344 879 and EP 0 384 050 describe face masks for use with a device for inhalation of aerosols. These face masks present a rather large "dead space" between the valve in the spacer and the face mask, requiring a certain inhalation flow to insure that the substance to be inhaled does not stay in this "dead space", but reaches the lung area. Moreover, the shape of these face masks is not adapted to the face of an infant as it is round and the inhalation device is to be held in a horizontal position which makes inhalation difficult for an infant. Thus neither of these two known devices is designed for the special needs of infants who are suffering from bronchial diseases.

SUMMARY OF THE INVENTION

The invention features, in one aspect, a face mask adapted to be mounted an inhalation device, e.g., an inhaler or spacer, having a body. The mask includes an annular adaptor part which is to be connected to one end of the body, and a funnel-shaped face engaging portion having a narrow end that is joined to one end of the adaptor part. The wide end of the face engaging portion has a free edge that is adapted to engage the face of an infant, around the infant's mouth and at least a part of the infant's nose, and is resilient so that it is adaptable to the shape of the infant's face.

The free edge of the wide end of the face engaging part is provided substantially in a plane which forms an angle of about 10°–25° with a plane perpendicular to the extended longitudinal axis of the adaptor part.

Advantageously, this inclination of the plane of the wide end of the face engaging portion makes it possible to minimize the dead space between the inhalation/exhalation valve and the mouth of the infant. Moreover, the inclination makes it natural for the user to hold the inhalation device in an inclined position in relation to the infant's face in a manner which corresponds to the inclination of a baby feeding-bottle during feeding, making use of the inhaler more comfortable for both the infant and the parent. The inclination also contributes to keeping the one way valve in the mouthpiece end of the spacer body of the inhalater opened, thus decreasing resistance during inhalation. As a result of the above advantages, inhalation by an infant or small child is significantly improved.

In another aspect, the invention features a method of treating an infant using inhalation therapy. The method includes: (a) providing a face mask according to the invention, (b) mounting the face mask on the mouthpiece of an inhalation device, (c) bringing the free edge of the face engaging portion into contact with the infant's face, and (d) using the inhalation device to deliver a medicament to the infant through the face mask.

The face mask according to the present invention is intended to be used by infants and young children up to the age of about 2.5 years. The word infant will be used herein to describe both an infant and a young child up to this age.

The face mask according to the invention is intended to be used in connection with a metered-dose aerosol inhaler for inhalation of aerosols, but could also be used together with any other inhalation device.

It is an object of the invention to provide a face mask for infants which overcomes the problems with the known face masks.

Other features and advantages of the invention will be apparent from the following description of preferred embodiments and from the claims.

DESCRIPTION OF THE PREFERRED EMBODIMENTS

Figure 1:
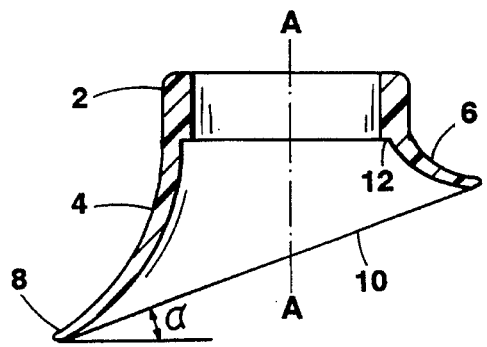
FIG. 1 shows a cross-sectional side view of a face mask according to one embodiment of the invention.

In FIG. 1 the face mask is shown in a side view. The face mask consists of two parts, a first part, the adaptor part 2, which is intended to be connected to the end of the spacer body of the inhalation device, e.g., inhaler or spacer, (not shown) and a second part, the face engaging portion 4, which is intended to be held against an infant's face during inhalation.

The adaptor part 2 is annular, preferably circular in cross-section, and has a length of preferably 12 mm. The thickness of the material in the adaptor part 2 is preferably about 5 mm.

The face engaging portion 4 is funnel-shaped and widens towards the free edge 10. The sides of the face engaging portion 4 are different in length, a short side 6 and a long side 8, as a consequence of the fact that the free edge 10 of the wide end of the face engaging portion is provided substantially in a plane which forms an angle α of about 10°–25°, preferably 15°–20°, with the plane perpendicular to the longitudinal axis A–A of the adaptor part 2.

The adaptor part 2 smoothly merges with the face engaging portion 4 without any sharp edges or seams. At the junction between the adaptor part 2 and face engaging portion 4 of the face mask a shoulder 12 is provided. This shoulder is placed at the point where the thickness of the adaptor part 2 decreases from preferably about 5 to about 2 –3 mm, which is the thickness of the fact engaging portion 4 at its base. The thickness of the material in the face engaging portion 4 decreases from about –3 mm at the junction with the adaptor part 2 to preferably about 0.5 mm at the free edge 10. On the short side 6 of the face engaging portion 4 a nose engaging part 14 is provided which is meant to at least partly cover the nose of the infant during inhalation. The length of the short side 6 is preferably about 20 mm including the adaptor part 2 and the length of the long side 8 is preferably about 48 mm including the adaptor part 2.

The outer contour of the walls of the funnel-shaped face engaging portion 4 is concave and preferably forms an arc of an circle where the radius of the long side 8 is preferably about 40 mm and the radius of the short side 6 is preferably about 16 mm. The inner contour of the walls is convex and preferably also forms an arc of an circle where the radius of the long side 8 is preferably about 38 mm and the radius of the short side 6 is preferably about 20 mm.

As the different radii of the outer and the inner contours respectively have different center points there will be a gradual decrease in thickness of the walls, tapering towards free edge 10.

The funnel-shaped face engaging portion 4 has an oval form to adapt to the form of an infant's face. The ratio between the major axis (B—B) and the minor axis (C—C) is thereby 1.2–1.4, see FIG. 2.

The free edge 10 and the adjacent part of the face engaging portion 4 are comparatively thin and therefore very flexible. When the face mask is placed around the mouth and at least part of the nose of an infant the outer part of the face engaging portion can therefore well adapt to the face of the infant so that if required the mask can seal against the face in an air tight manner. This is especially important when the substance to be inhaled comprises steroids or other substances with which the eyes must not come into contact.

Figure 2:
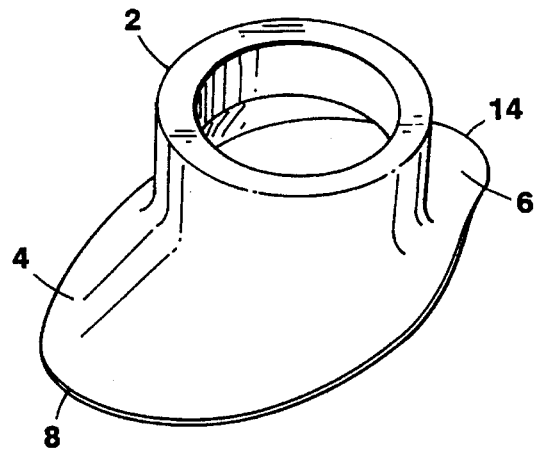
FIG. 2 shows a top view of the face mask shown in FIG. 1.
Figure 3:
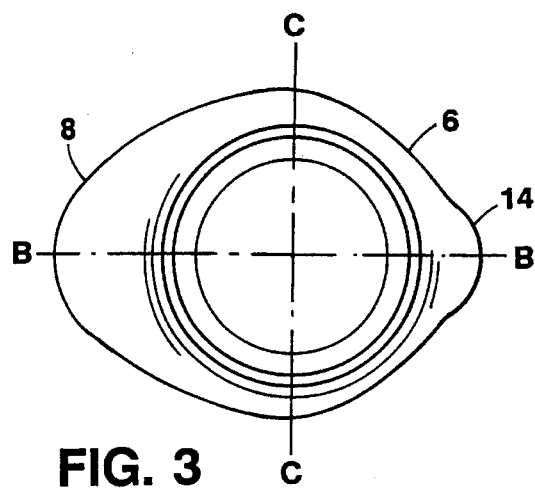
FIG. 3 is a perspective view of the face mask shown in FIG. 1.

As can be seen in FIG. 2 the nose engaging part 14 can be shaped as a substantial semi-circular protrusion extending from the edge of the short side 6. With this protrusion the adaption to the nose of the infant is improved.

Figure 4:
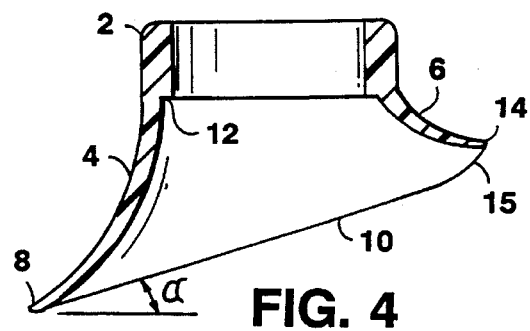
FIG. 4 shows a cross-sectional side view of a face mask according to an alternate embodiment of the invention.
Figure 4A:
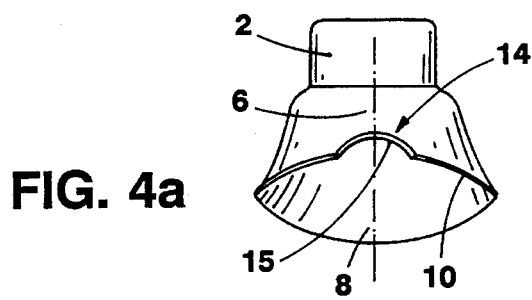
FIG. 4a shows a front view of the face mask shown in FIG. 4.

The nose engaging part 14 could also be provided with a more inclined edge 15 to better adapt to the shape of an infant's nose. The inclined edge 15 of the nose engaging part, which curves upwards and backwards towards the adaptor part 2 as shown in FIGS. 4 and 4a.

The mask according to the invention is preferably made of thermoplastic material or other rubber-like material that is soft and resilient such as thermoplastic elastomers or silicon-like materials. Of course other materials having similar properties could also be used.

Reference has been made herein to treatment of asthmatic diseases by inhalation of suitable medical substances, but it is apparent that the face mask according to the invention also could be used for inhalation of other medical substances, such as for example anesthetics.

Reference is also made to the use of the face mask together with metered-dose aerosol inhalers, but the face mask could also be used together with any kind of inhalers provided that they have an adaptor part at their mouthpiece end adapted to fit to the adaptor part of the face mask.

Other embodiments are within the claims.

For example, the inside of the adaptor part, which in the above described embodiment is provided with a shoulder in the transition between the adaptor part and the face engaging portion, could smoothly merge into the face engaging part.

Further, although it is not necessary, as the material and the thinness of the edge of the face mask makes it possible for exhalation air to escape from the face mask and the inhaler, the face engaging portion could be provided with an exhalation hole to make the escape of the exhaled air easier during the inhalation treatment.

Although it is preferred that the adaptor part and face-engaging portion comprise a single unitary part, as shown, alternatively the two parts could be formed separately and joined.

We claim:

1. A face mask for an infant, said face mask being adapted to be mounted on an inhalation device having an end dimensioned to deliver a medicament during inhalation, said mask comprising:

an adaptor part having a first end which is dimensioned to be connected to the end of the inhalation device; and a face engaging portion having a narrow end which is adjacent a second end of the adaptor part opposite said first end and a wide end having a free edge which is adapted to engage an area around the mouth and at least a part of the nose of an infant, said free edge being resilient to be adaptable to said area;

wherein said free edge defines and is disposed substantially entirely in a plane which forms an angle of about 20°–25° with a plane perpendicular to the extended longitudinal axis of the adaptor part.

2. A face mask of claim 1, wherein the thickness of the wall of the face engaging portion decreases gradually outwardly towards the free edge of the face engaging portion.

3. A face mask of claim 1, wherein the face mask is made of a thermoplastic material.

4. A face mask of claim 1, wherein the free edge of the face engaging portion is oval.

5. A face mask of claim 4, wherein the ratio between the major axis and the minor axis of the oval is 1.2–1.4.

6. A face mask of claim 1, wherein the outer side of the adaptor part smoothly merges with the outer side of the face engaging portion.

7. A face mask according to claim 1 or 6, wherein a shoulder is provided on the inner surface of the face mask where the adaptor part and the face engaging portion meet.

8. A face mask of claim 1 or 6 wherein the adaptor part and face engaging portion comprise a single, unitary member.

9. A face mask of claim 1 wherein the outer surface of the face engaging portion is concave.

10. A face mask of claim 9 wherein the outer surface describes an arc of an circle.

11. A face mask of claim 1 or 9 wherein the inner surface of the face engaging portion is convex.

12. A face mask of claim 11 wherein the inner surface describes an arc of an circle.

13. A face mask of claim 1 wherein said face engaging portion includes a short side, a portion of which is dimensioned to be positioned against the nose of an infant, and a long side, dimensioned to be positioned below the mouth of an infant.

14. A face mask of claim 13, wherein a nose engaging part of the face mask is provided at the short side of the face engaging portion.

15. A face mask of claim 14, wherein a protrusion is provided on the nose engaging part of the face engaging portion.

16. A face mask of claim 15, wherein the protrusion is substantially semi-circular.

17. The face mask of claim 15 wherein said protrusion extends out of the plane defined by the face-engaging portion.

18. A face mask of claim 15 or 16 wherein the protrusion includes an inclined edge which curves away from the plane defined by the free edge and towards the adaptor part.

19. A method of treating an infant by delivering a medicament through an inhalation device having a first end adapted to deliver the medicament during inhalation, said method comprising the steps of:
   a) providing a face mask comprising
      an adaptor part having a first end which is dimensioned to be connected to said first end of the inhalation device; and
      a face engaging portion having a narrow end which is adjacent a second end of the adaptor part, opposite said first end, and a wide end having a free edge which is adapted to engage an area around the mouth and at least a part of the nose of an infant and being resilient to be adaptable to said area;
      the free edge defining and being disposed substantially entirely in a plane which forms an angle of about 10°–25° with a plane perpendicular to the extended longitudinal axis of the adaptor part;
   b) mounting the face mask on the first end of the inhalation device;
   c) bringing the free edge of the face engaging portion into contact with said area of an infant's face; and
   d) using the inhalation device to deliver a medicament to an infant through the face mask.

20. A method of claim 19 further comprising the step of bringing the free edge into sealing contact with an infant's face.

21. A method of claim 19, wherein said step of providing a face mask comprises providing the face engaging portion with a nose engaging portion dimensioned to engage the nose of an infant, and bringing the nose engaging portion into contact with a portion of an infant's nose.

22. A face mask for an infant, said face mask being adapted to be mounted on an inhalation device having an end capable of delivering a medicament during inhalation, said mask comprising:
   an adaptor part a first end of which is dimensioned to be connected to the end of the body of the inhalation device; and
   a face engaging portion having a narrow end which is adjacent a second end of the adaptor part opposite said first end and a wide end having a free edge which is adapted to engage an area around the mouth and at least a part of the nose of an infant, said free edge being resilient to be adaptable to said area;
   wherein substantially all of said free edge is disposed in a plane which forms an angle of about 10°–25° with a plane perpendicular to the extended longitudinal axis of the adaptor part, a nose engaging portion is provided at the short side of the face engaging portion, and the adaptor part has a cylindrical inner surface and protrudes from the narrow end of the face engaging portion.

23. A face mask for an infant, said face mask being adapted to be mounted on an inhalation device having an end capable of delivering a medicament during inhalation, said face mask comprising:
   an adaptor part having a first end which is dimensioned to be connected directly to the end of the inhalation device; and
   a face engaging portion having a narrow end which is adjacent a second end of the adaptor part which is opposite said first end, and a wide end having a free edge which is adapted to engage an area around the mouth and at least a part of the nose of an infant, said free edge being resilient to be adaptable to said area;
   wherein substantially all of said free edge is disposed in a plane which forms an angle of about 10°–25° with a plane perpendicular to the extended longitudinal axis of the adaptor part, said plane in which said free edge lies being inclined in a direction, with respect to the longitudinal axis of the adaptor part, that allows the user to hold the inhalation device in an inclined position in relation to the infant's face in a manner which corresponds to the inclination of a baby feeding-bottle during feeding, and said adaptor part being adapted to restrict movement of the inhalation device within the adaptor part during use.

* * * * *